United States Patent [19]

Kai et al.

[11] Patent Number: 4,543,602
[45] Date of Patent: Sep. 24, 1985

[54] SURFACE INSPECTION METHOD

[75] Inventors: Tooru Kai, Inazawa; Chikahisa Hayashi, Anzou, both of Japan

[73] Assignee: Toyoda Gosei Co., Ltd., Nishikasugai, Japan

[21] Appl. No.: 489,970

[22] Filed: Apr. 29, 1983

[30] Foreign Application Priority Data

Apr. 30, 1982 [JP] Japan .................................. 57-74057

[51] Int. Cl.$^4$ ............................................... H04N 7/18
[52] U.S. Cl. ..................................... 358/106; 356/398; 358/93
[58] Field of Search ................. 358/106, 107, 93, 101; 356/394, 398

[56] References Cited

U.S. PATENT DOCUMENTS 3,794,427 2/1974 Shibata .................................. 356/394
3,976,382 8/1976 Westby .................................. 356/398
4,352,430 10/1982 Maier .................................. 358/106

Primary Examiner—Howard W. Britton
Attorney, Agent, or Firm—Cushman, Darby & Cushman

[57] ABSTRACT

In a surface inspection method in which parallel rays passing through a thin slit are projected onto a surface of a specimen and a luminous line formed on the specimen surface by the parallel rays is viewed by a television camera so as to inspect the specimen surface, a photo-electric signal showing the luminous line is picked up from an output video signal of the television camera. The time from rising state of the horizontal synchronizing signal contained in the video signal to occurrence of a pulse of the photo-electric signal is measured in each period of the horizontal synchronizing signal. The time data in each period is compared with a previously set reference value, and whether or not the specimen passes the inspection is discriminated based on variation of the comparison result.

2 Claims, 4 Drawing Figures

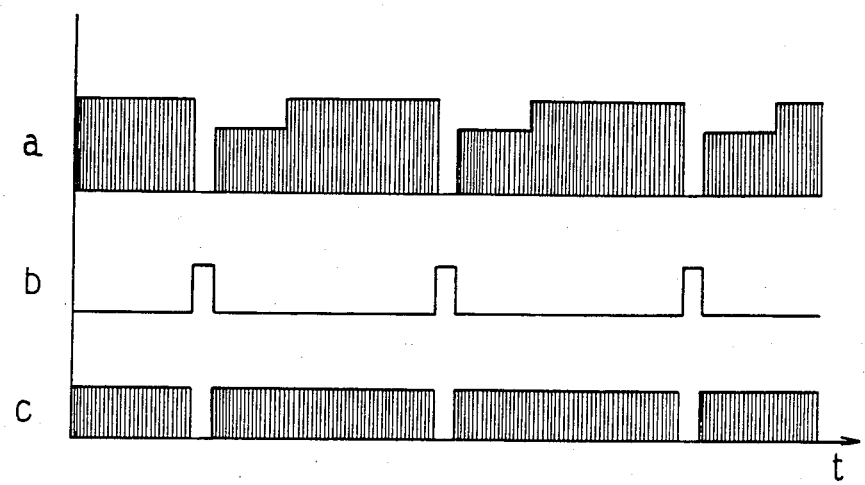
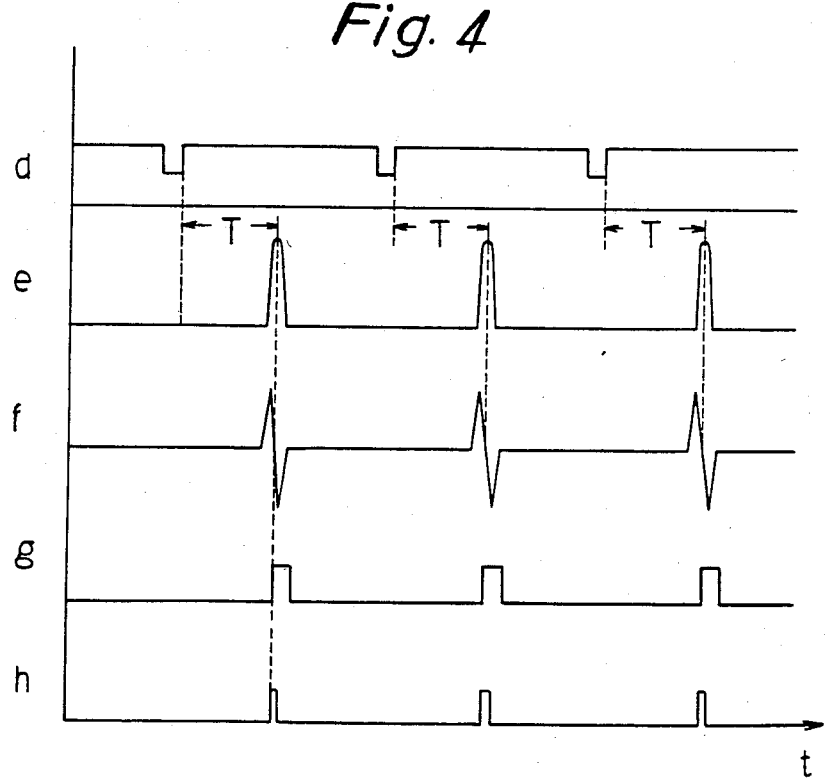

SURFACE INSPECTION METHOD

BACKGROUND OF THE INVENTION

1. Field of the Invention

This invention relates to a surface inspection method wherein a surface of a rubber or metal formed product is viewed by a television camera (video camera) and roughness or cracks of the specimen surface is inspected.

2. Description of the Prior Art

In conventional methods for inspecting roughness or cracks of surfaces of rubber or metal formed product, parallel rays passing through a thin slit are projected onto a surface of a specimen and the specimen surface is illuminated by parallel rays. Observation by visual inspection from the lateral side is carried out, whereby surface unevenness is determined from the contour of luminous lines visible on the surface. However, this method has disadvantages in that a demanding inspection technique is required in the visual inspection and the inspection work is time-consuming. Moreover, the method has disadvantages in that a luminous line formed by the projected rays becomes broad when inspecting a curved surface portion and that unequal brightness of parallel rays causes unequal brightness of the luminous line, resulting in reduction of accuracy of the inspection.

SUMMARY OF THE INVENTION

An object of this invention is to provide a surface inspection method wherein inspection of the surface of a specimen is carried out automatically and efficiently.

Another object of this invention is to provide a surface inspection method wherein the inspection work is not affected appreciably by surface configuration of a specimen or light rays and stable inspection accuracy is obtained.

In order to attain the above-mentioned objects, this invention provides a surface inspection method wherein parallel rays passing through a thin slit are projected onto the surface of a specimen, and a luminous line formed on the specimen surface by the parallel rays is viewed by a television camera. The inspection method comprises the step of picking up a photo-electric signal showing the luminous line from an output video signal of the television camera, the step of measuring the time from the rising state of a horizontal synchronizing signal contained in the video signal, to the occurrence of the pulse of the photo-electric signal in each period of the horizontal synchronizing signal, and the step of comparing the time data in each period with a previously set reference value so as to discriminate the surface of the specimen.

BRIEF DESCRIPTION OF THE DRAWINGS

FIGS. 3 and 4 are wave-form charts in circuits of the surface inspecting device.

DESCRIPTION OF THE PREFERRRED EMBODIMENT

An embodiment of this invention will now be described referring to the accompanying drawings.

Figure 1:
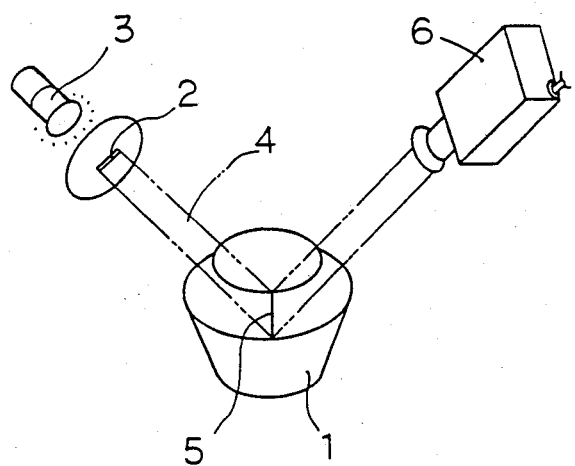
FIG. 1 is a view illustrating a method of surface inspection according to an embodiment of this invention.
Figure 2:
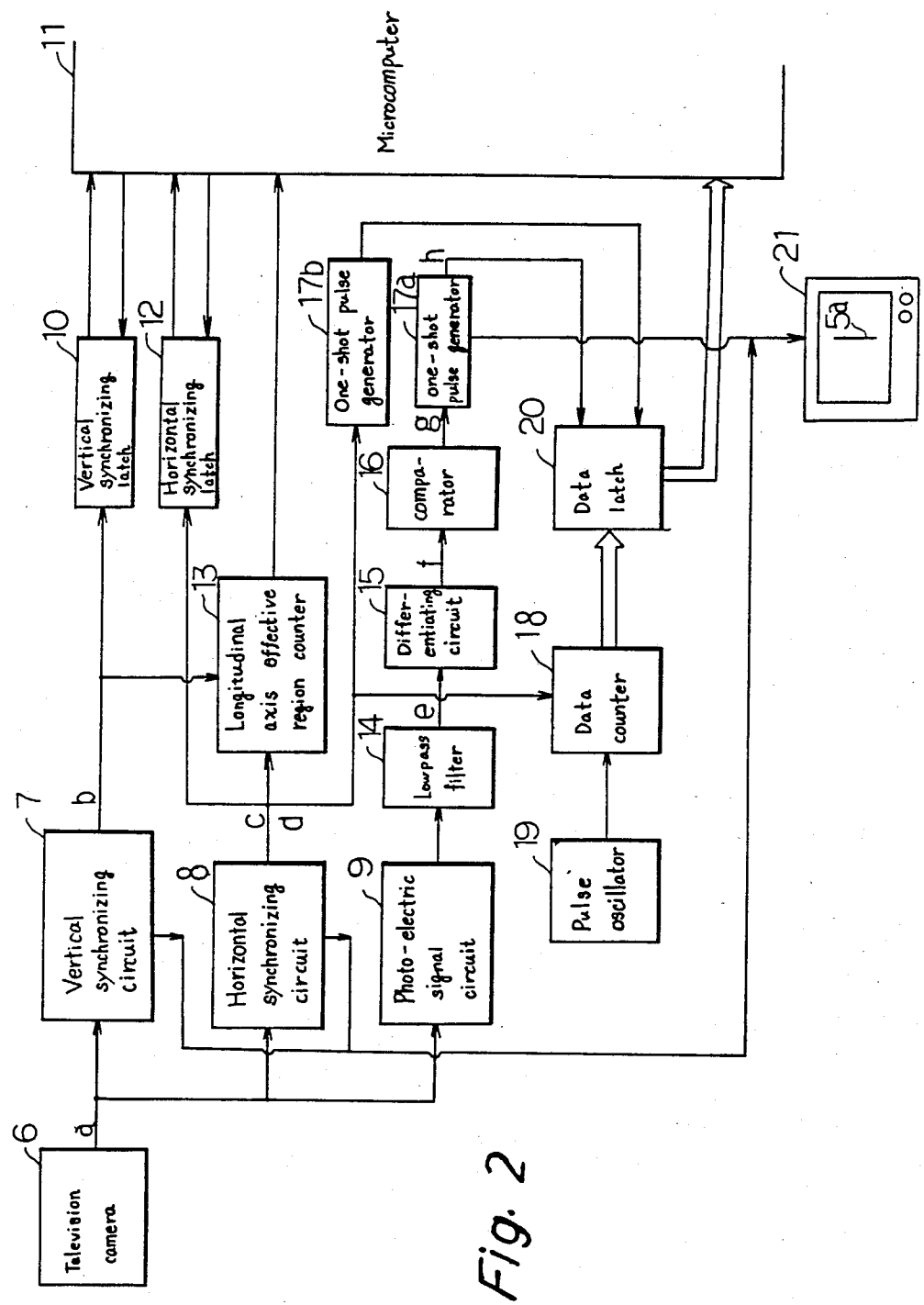
FIG. 2 is a block diagram of a surface inspecting device.

FIG. 1 is a diagram illustrating an arrangement of the surface inspection method of this invention, and FIG. 2 is a block diagram of a surface inspecting device. Reference numeral 1 designates a specimen being a molded product of rubber. A thin slit 2 and a light source 3 for projecting the usual light ray or laser ray through the slit 2 are disposed above the specimen 1. Parallel rays 4 which pass through the thin slit 2 illuminate the surface of the specimen 1, whereby a luminous line 5 is formed on the surface. The luminous line 5 is viewed by a television camera 6 disposed on lateral side of the specimen 1. A zoom lens is used in the television camera 6 so as to make the setting easy.

The output side of the television camera 6 is connected to a vertical synchronizing circuit 7, a horizontal synchronizing circuit 8 and a photo-electric signal circuit 9, as shown in FIG. 2. The vertical synchronizing circuit 7 picks up the vertical synchronizing signal separately from the video signal outputted by the television camera 6, and the horizontal synchronizing circuit 8 picks up the horizontal synchronizing signal separately from the video signal. The photo-electric signal circuit 9 sets a threshold voltage from the video signal, and picks up a photo-electric signal having information therein of brightness and darkness. Numeral 10 designates a vertical synchronizing latch for adjusting the timing of the vertical synchronizing signal to be transmitted to a microcomputer 11. The vertical synchronizing latch 10 receives the vertical synchronizing signal from the vertical synchronizing circuit 7, transmits it to the microcomputer 11, and then is reset by a reset signal from the microcomputer 11. Numeral 12 desingates a horizontal synchronizing latch for adjusting the timing of the horizontal synchronizing signal to be transmitted to the microcomputer 11. The horizontal synchronizing latch 12 receives the horizontal synchronizing signal from the horizontal synchronizing circuit 8, transmits it to the microcomputer 11, and then is reset by a reset signal from the microcomputer 11.

Numeral 13 designates a longitudinal axis effective counter for releasing a dummy region and outputting an inspection effective region to the computer 11. The longitudinal axis effective counter 13 is connected to the vertical synchronizing circuit 7 and to the horizontal synchronizing circuit 8. The longitudinal axis effective counter 13 receives the horizontal synchronizing signal and counts it, and if the count number attains a prescribed inspection effective region (for example, No. 30-300 in the horizontal synchronizing signal), a pulse signal is outputted to the microcomputer 11 and the counter is reset on receiving the vertical synchronizing signal.

Numeral 14 designates a lowpass filter connected to the photo-electric signal circuit 9 for removing high-frequency components contained in the photo-electric signal. The photo-electric signal passes through the low-pass filter 14 and is transmitted to a differentiating circuit 15, and the differentiation photo-electric signal differentiated there is transmitted to a comparator 16. The comparator 16 compares the differentiation photo-electric signal with 0 volt, and detects the transferring point where the differentiation photo-electric signal is changed from a positive value to a negative value. The pulse signal rising at the transferring point is fed to a one-shot pulse generator 17a. The one-shot pulse generator 17a generates a pulse signal of short time-width in response to signal from the comparator 16 and feeds it as latch signal to a data latch 20.

Numeral 18 designates a data counter for receiving a clock pulse signal from a pulse oscillator 19 and a horizontal synchronizing signal from the horizontal synchronizing circuit 8. The data counter 18 is reset at rising by the input of the horizontal synchronizing signal, counts the number of pulse signals from the pulse oscillator 19 until the input of the next horizontal synchronizing signal, and transmits data of the count value to the data latch 20. The data latch 20 receives a data signal from the data counter 18 and also receives a pulse signal as a latch signal outputted from both one-shot pulse generators 17a and 17b connected respectively to the comparator 16 and the horizontal synchronizing circuit 8. The data latch 20 latches the data signal and transmits it to the microcomputer 11. Numeral 21 designates a CRT monitor display which receives the one-shot pulse signal of the one-shot pulse generator 17a, the vertical synchronizing signal, and the horizontal synchronizing signal, and synthesizes them to form a monitor image.

Referring to wave-form charts in FIGS. 3 and 4, the method of surface inspection will now be described together with operation of a surface inspection device.

Parallel rays 4 are projected from the light source 3 through the slit 2 onto the surface of the specimen 1 in a normal position. Brilliant light line 5 formed thereby on the surface of the specimen 1 is viewed by the television camera 6 vertically on an almost full display field. Video signal a (FIG. 3) produced by the television camera 6 is transmitted to the vertical synchronizing circuit 7, the horizontal synchronizing circuit 7 and the photo-electric signal circuit 9. The vertical synchronizing circuit 7 picks up vertical synchronizing circuit 8 separates horizontal synchronizing signal c, and the photo-electric signal circuit 9 sets a threshold voltage and separates the photo-electric signal from the video signal.

The vertical synchronizing signal b from the vertical synchronizing circuit 7 passes through the vertical synchronizing latch 10 and is converted into a timing signal of suitable width (for data input processing) based on the horizontal synchronizing signal b, and the timing signal is transmitted to the microcomputer 11. The horizontal synchronizing signal c from the horizontal synchronizing circuit 8 passes through the horizontal synchronizing latch 12, is converted into a timing signal for data input processing, and the timing signal is transmitted to the microcomputer 11. The longitudinal axis effective region counter 13 is supplied with horizontal synchronizing signal c and vertical synchronizing signal b. The longitudinal axis effective region counter 13 is reset by the vertical synchronizing signal and counts the number of horizontal synchronizing signals. A command signal is outputted to the microcomputer 11 so that horizontal synchronizing signals from No. 30 to No. 300, for example, are in the longitudinal axis effective region and others are in the dummy region, and data processing is carried out in the effective region.

A photo-electric signal separated from video signal a is outputted by the photo-electric signal circuit 9, and passes through the low-pass filter 14, whereby high-frequency components are removed and a pulse signal indicating the brilliant line in the display field can be picked up as shown in wave-form e of FIG. 4. The photo-electric signal e is fed to the differentiating circuit 15 and differentiated there, and the differentiation photo-electric signal f is entered in the comparator 16.

The comparator 16 compares the differentiation photo-electric signal f with a potential of 0 volt and detects the transferring point where the signal f is changed from a positive value to a negative value. Pulse signal g rising at the transferring point is applied to the one-shot pulse generator 17a. Then, the one-shot pulse generator 17a outputs pulse signal h having narrow time-width in synchronization with the rising of the input pulse signal, and the pulse signal h is transmitted as a latch signal to the data latch 20.

The data counter 18 receives the horizontal synchronizing signal d reset signal and counts clock pulse signals from the pulse oscillator 19; and if latch signal is applied to the data latch 20 the count value is latched. Referring to FIG. 4, the count value represents the time T from rising state of one pulse of the horizontal synchronizing signal d to the center of a pulse wave-form corresponding to the luminous line 5 obtained by differentiating the photo-electric signal e. Since the time T is that from generation of one pulse of a horizontal synchronous signal to generation of the photo-electric signal showing the luminous line 5, i.e., brilliant line, if the luminous line 5a taken vertically by the television camera 6 is straight, the count value obtained in each period, i.e., the time, becomes constant. However, if a defect is present on the surface of the specimen 1 and therefore the contour or shape of the image of the luminous line viewed by the television camera 6 is bent on account of the recess of the defect, data including a different count value partly among the data as a whole is picked up.

In this arrangement, each data of the count value latched in the data latch 20 is fed sequentially to the microcomputer 11. The microcomputer 11 compares each data with a previously set reference value and thereby estimates the variation. Based on the estimated variation, discrimination is effected regarding whether or not the specimen 1 passes the inspection. If the difference of each data from the reference value becomes beyond a prescribed value, discrimination is effected that the specimen is off-grade. In an upper or lower portion of the display field, the luminous line 5a is not displayed, but a pulse signal outputted from the one-shot pulse generator 17b per each pulse in the horizintal synchronizing signal d is applied as a latch signal to the data latch 20. Data of the count value in this case corresponds to one period of the horizontal synchronizing signal and is not processed as data of the luminous line 5a in the microcomputer 11.

An image of the specimen being inspected is displayed on a monitor display 21, and pulse signal h with shaped wave outputted from the one-shot pulse generator 17a is used as a photo-electric signal in the video signal, whereby a clear image without fade can be produced and defects in the specimen can be clearly shown even in a visual inspection.

If surface inspection is effected in such a specimen such that the luminous line is slanted or bent midway, the camera is set accurately so that the luminous line is displayed at a prescribed position on the CRT. The time of each synchronizing signal until generation of a photo-electric signal is previously stored in a memory or the like, each detected data is compared with above-mentioned setting time, and whether or not the specimen passes the inspection is discriminated based on the comparison result.

According to the surface inspection method of this invention as above described, parallel rays passing through a thin slit are projected onto the surface of a specimen, and a luminous line formed on the specimen surface by the parallel rays is viewed by a television camera. The surface inspection method comprises the step of picking up a photo-electric signal showing the luminous line from the video signal of the television camera, the step of measuring the time from rising state of the horizontal synchronizing signal contained in the video signal to the pulse of a photo-electric signal in each period of the horizontal synchronizing signal, and the step of comparing the time data in each period with a previously set reference value so as to discriminate the surface of the specimen. This invention provides an arrangement wherein surface inspection work of rubber, metal formed product or the like can be carried out under mechanization without necessitating workers highly skilled in inspection techniques, inspection is carried out simply and efficiently in comparison to conventional visual inspection, and stable inspection accuracy is obtained without being appreciably affected by the surface configuration of the specimen and light rays.

What is claimed is:

1. A surface inspection method wherein parallel rays passing through a thin slit are projected onto a surface of a specimen, and a luminous line formed on the specimen surface by the parallel rays is viewed by a television camera whereby surface inspection of the specimen is carried out, said surface inspection method comprising:

(a) the step of picking up a photo-electric signal showing the luminous line from an output video signal of the television camera, said photo-electric signal being converted into a differentiation photo-electric signal by a differentiating circuit, and the differentiation photo-electric signal being converted into a pulse signal of small width rising at the transferring point from positive value to negative value, producing a pulse signal whose rising point is the zero-crossing point of said differentiated photo-electric signal;
   (b) the step of measuring a time from a rising state of a horizontal synchronizing signal contained in the video signal to occurrence of a pulse of the photo-electric signal in each period of the horizontal synchronizing signal; and
   (c) the step of comparing the time data in each period with a previously set reference value and discriminating whether or not the specimen passes the inspection based on variation of the comparison result.

2. A surface inspection method according to claim 1, characterized in that a longitudinal axis effective region of the horizontal synchronizing signal contained in the video signal is set, and the time from the rising state of the horizontal synchronizing signal in each period to the pulse of the photo-electric signal is measured within the longitudinal axis effective region.

* * * * *